(12) United States Patent
Holmes et al.

(10) Patent No.: US 12,616,620 B1
(45) Date of Patent: May 5, 2026

(54) DIAPER WITH INTEGRATED DISPOSAL SYSTEM

(71) Applicants: Bruce Holmes, Lawrenceville, GA (US); Letitia Garner, Lawrenceville, GA (US)

(72) Inventors: Bruce Holmes, Lawrenceville, GA (US); Letitia Garner, Lawrenceville, GA (US)

( * ) Notice: Subject to any disclaimer, the term of this patent is extended or adjusted under 35 U.S.C. 154(b) by 505 days.

(21) Appl. No.: 18/075,563

(22) Filed: Dec. 6, 2022

(51) Int. Cl.
| | |
|---|---|
| *A61F 13/551* | (2006.01) |
| *A61F 13/49* | (2006.01) |
| *A61F 13/494* | (2006.01) |
| *A61F 13/495* | (2006.01) |
| *A61F 13/51* | (2006.01) |
| *A61F 13/513* | (2006.01) |
| *A61F 13/53* | (2006.01) |
| *A61F 13/537* | (2006.01) |
| *A61F 13/56* | (2006.01) |
| *A61F 13/84* | (2006.01) |

(52) U.S. Cl.
CPC .... *A61F 13/5512* (2013.01); *A61F 13/49011* (2013.01); *A61F 13/49413* (2013.01); *A61F 13/495* (2013.01); *A61F 13/51311* (2013.01); *A61F 13/53708* (2013.01); *A61F 13/5638* (2013.01); *A61F 13/8405* (2013.01); *A61F 2013/49093* (2013.01); *A61F 2013/4958* (2013.01); *A61F 2013/5103* (2013.01); *A61F 2013/51033* (2013.01); *A61F 2013/530489* (2013.01); *A61F 2013/530547* (2013.01); *A61F 2013/55125* (2013.01); *A61F 2013/8408* (2013.01)

(58) Field of Classification Search
CPC .............. A61F 13/551; A61F 13/55115; A61F 13/5512; A61F 2013/55125; A61F 2013/55195
USPC ........................................ 604/385.13, 385.19
See application file for complete search history.

(56) References Cited

U.S. PATENT DOCUMENTS

| | | | | |
|---|---|---|---|---|
| 3,369,545 A | * | 2/1968 | Wanberg | ............... A61F 13/551 604/366 |
| 3,731,689 A | * | 5/1973 | Schaar | .................. A61F 13/551 604/371 |
| 3,865,110 A | * | 2/1975 | Traverse | ............... A61F 13/551 604/385.13 |
| 5,071,414 A | * | 12/1991 | Elliott | .................. A61F 13/551 604/385.13 |

(Continued)

FOREIGN PATENT DOCUMENTS

| | | | | |
|---|---|---|---|---|
| WO | 96/19166 | * | 6/1996 | ............. A61F 13/15 |
| WO | 2010103516 | | 9/2010 | |

*Primary Examiner* — Michele Kidwell
(74) *Attorney, Agent, or Firm* — Kyle A. Fletcher, Esq.

(57) ABSTRACT

The diaper with integrated disposal system comprises a disposable diaper and a disposal bag. The disposable diaper may be adapted to be worn by a baby to retain waste, and mask odor. As a non-limiting example, the waste may be urine and/or feces. The disposal bag may be coupled to the outside of the back of the disposable diaper, as worn, such that the disposal bag is kept clean and available at all times. The disposable diaper containing the waste may be referred to as a soiled diaper. The soiled diaper may be removed from the baby and rolled to contain the waste. The disposal bag may be pulled around the soiled diaper to seal the soiled diaper within the disposal bag.

16 Claims, 4 Drawing Sheets

(56)                    References Cited

U.S. PATENT DOCUMENTS

| | | | |
|---|---|---|---|
| 5,151,092 A * | 9/1992 | Buell | ................ A61F 13/15707 |
| | | | 604/385.3 |
| 5,318,554 A * | 6/1994 | Young | ............... A61F 13/49009 |
| | | | 604/374 |
| D596,287 S | 7/2009 | Tan | |
| 8,858,521 B2 | 10/2014 | Karsenti | |
| 8,870,841 B2 | 10/2014 | Tavolacci | |
| 9,532,911 B2 | 1/2017 | Amiri | |
| 11,123,231 B2 | 9/2021 | Lee | |
| 2005/0182375 A1* | 8/2005 | Kropf | ................. A61F 13/5512 |
| | | | 604/385.01 |
| 2013/0110072 A1 | 5/2013 | Carvalho | |
| 2016/0038352 A1 | 2/2016 | Greene | |
| 2019/0350776 A1* | 11/2019 | Roszkowiak | ....... A61F 13/5512 |
| 2020/0093658 A1 | 3/2020 | Copeland | |

* cited by examiner

DIAPER WITH INTEGRATED DISPOSAL SYSTEM

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of diapers, more specifically, a diaper with integrated disposal system.

SUMMARY OF INVENTION

The diaper with integrated disposal system comprises a disposable diaper and a disposal bag. The disposable diaper may be adapted to be worn by a baby to retain waste. As a non-limiting example, the waste may be urine and/or feces. The disposal bag may be coupled to the outside of the back of the disposable diaper, as worn, such that the disposal bag is kept clean and available at all times. The disposable diaper containing the waste may be referred to as a soiled diaper. The soiled diaper may be removed from the baby and rolled to contain the waste. The disposal bag may be pulled around the soiled diaper to seal the soiled diaper within the disposal bag, and also to mask odor.

An object of the invention is to provide a disposable diaper.

Another object of the invention is to provide a disposal bag for bagging a soiled disposable diaper.

Yet another object of the invention is to provide a disposal bag that masks odor associated with the soiled diaper.

A further object of the invention is to couple the disposal bag to the outside rear of the disposable diaper.

Yet another object of the invention is to provide a disposal bag that may be inverted by pulling an elastic pouch band down from the rear, under the soiled diaper, and up over the front of the soiled diaper to envelope the soiled diaper within the disposal bag.

These together with additional objects, features and advantages of the diaper with integrated disposal system will be readily apparent to those of ordinary skill in the art upon reading the following detailed description of the presently preferred, but nonetheless illustrative, embodiments when taken in conjunction with the accompanying drawings.

In this respect, before explaining the current embodiments of the diaper with integrated disposal system in detail, it is to be understood that the diaper with integrated disposal system is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the diaper with integrated disposal system.

It is therefore important that the claims be regarded as including such equivalent construction insofar as they do not depart from the spirit and scope of the diaper with integrated disposal system. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description. As used herein, the word "or" is intended to be inclusive.

Figure 1:
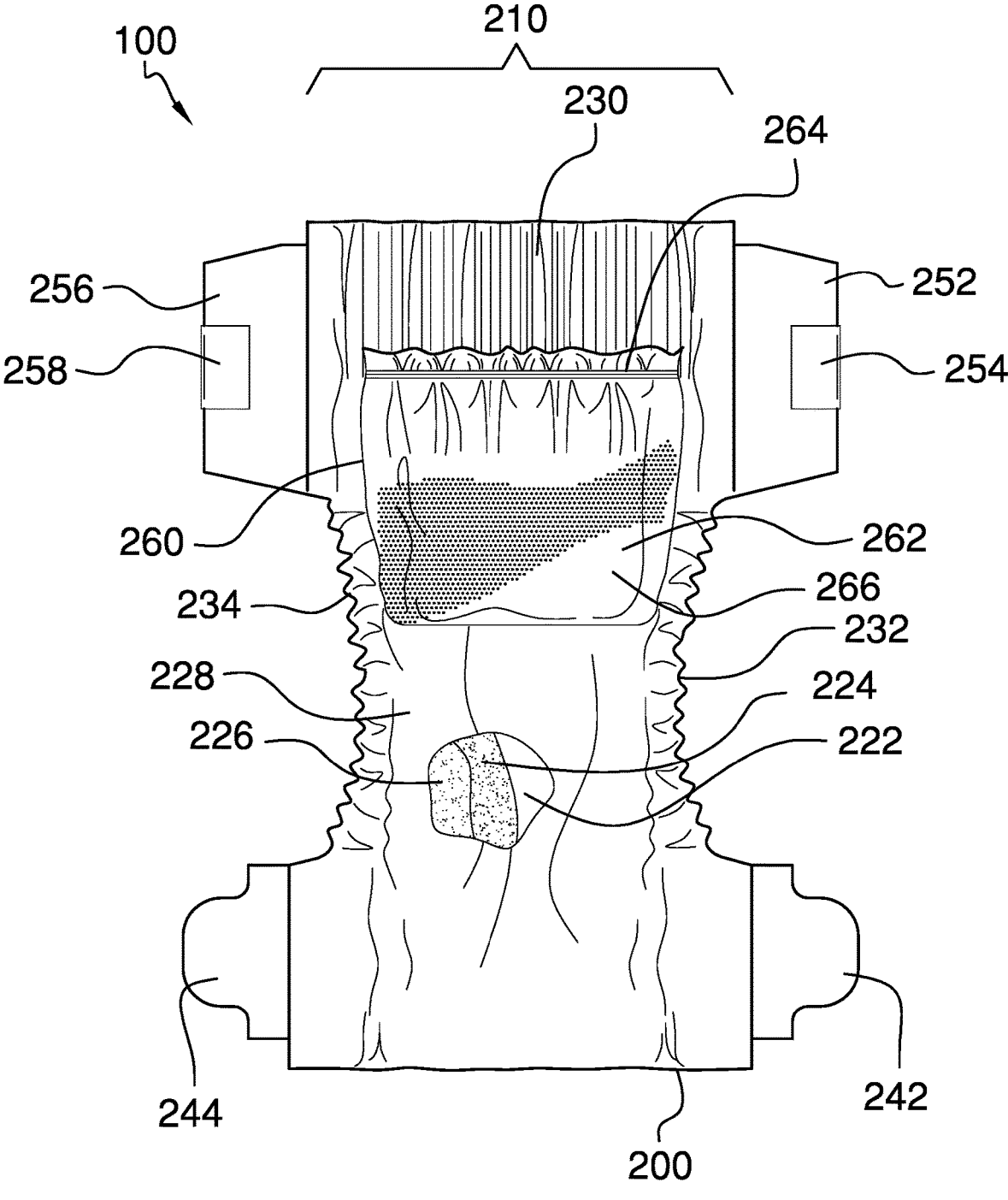
FIG. 1 is a top view of an embodiment of the disclosure, illustrating the outside layer of the diaper with integrated disposal system.
Figure 2:
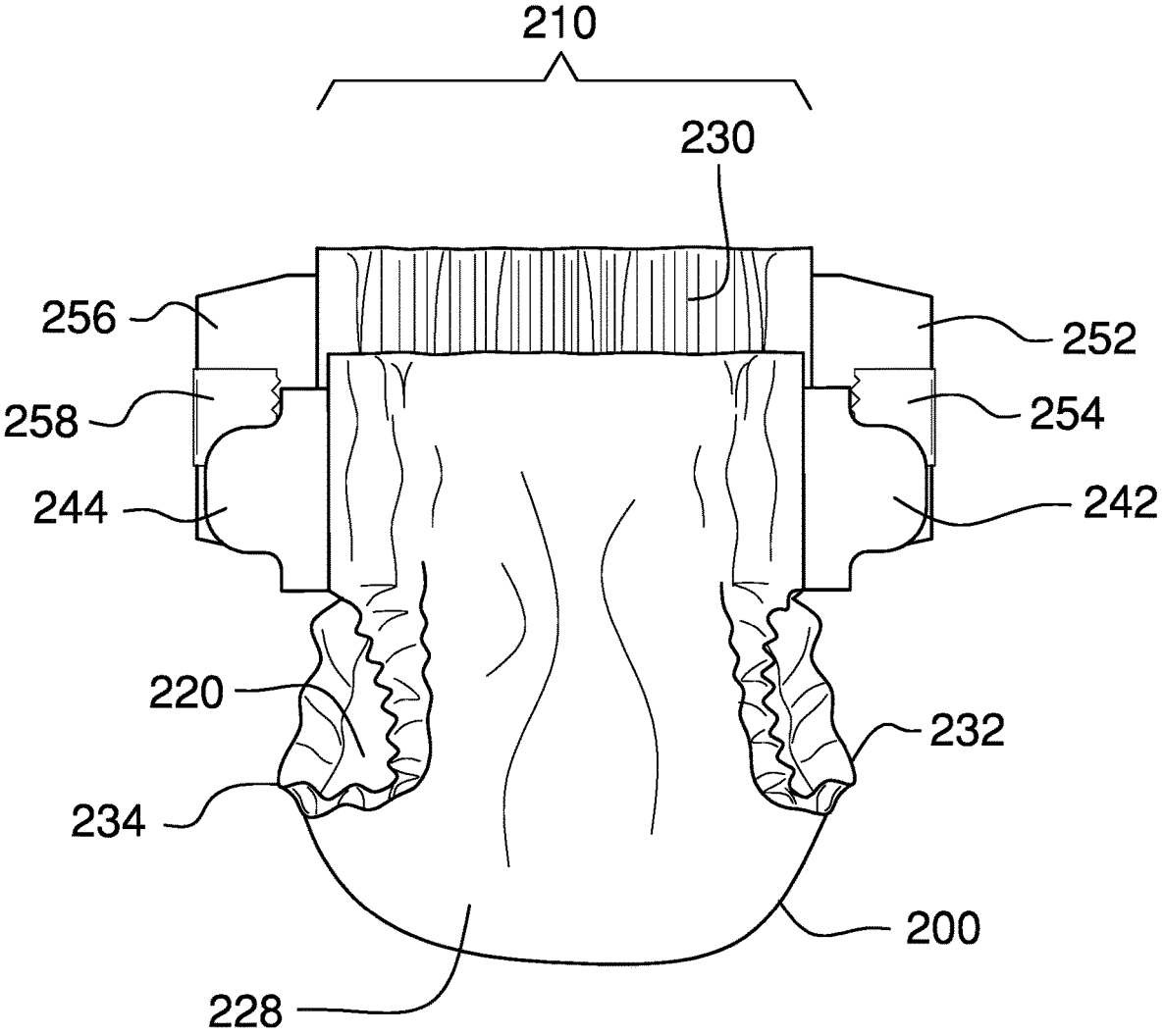
FIG. 2 is a front view of an embodiment of the disclosure as worn.
Figure 3:
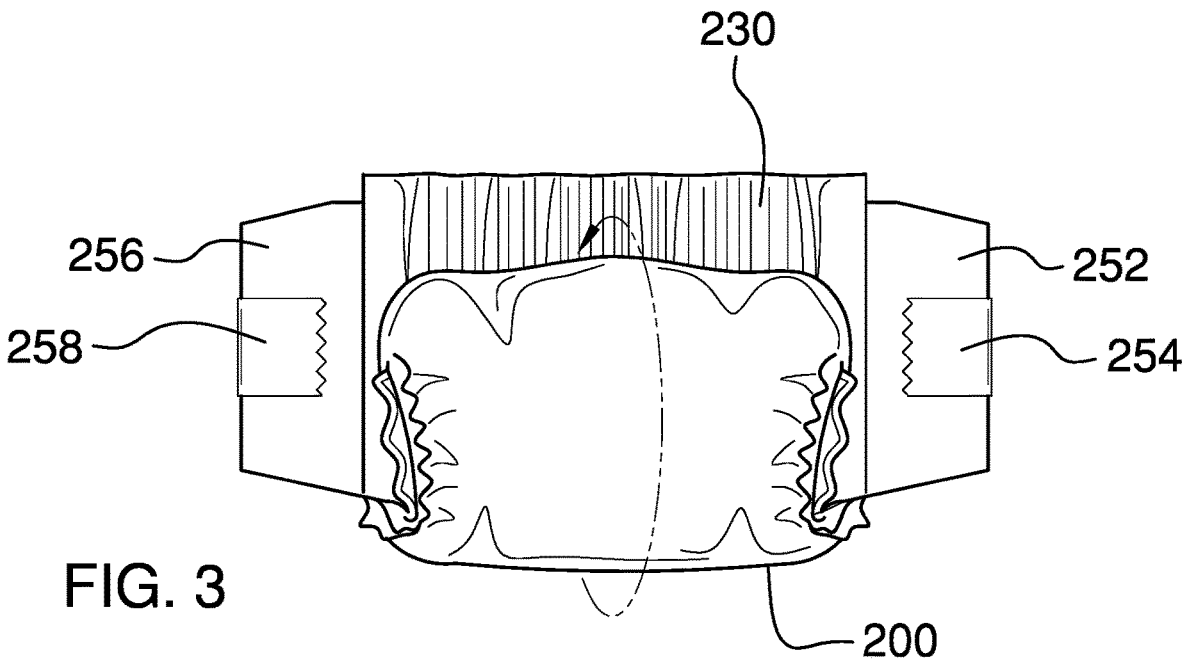
FIG. 3 is a front view of an embodiment of the disclosure, as worn, illustrating the stop of rolling a soiled diaper up from the front of the diaper.
Figure 4:
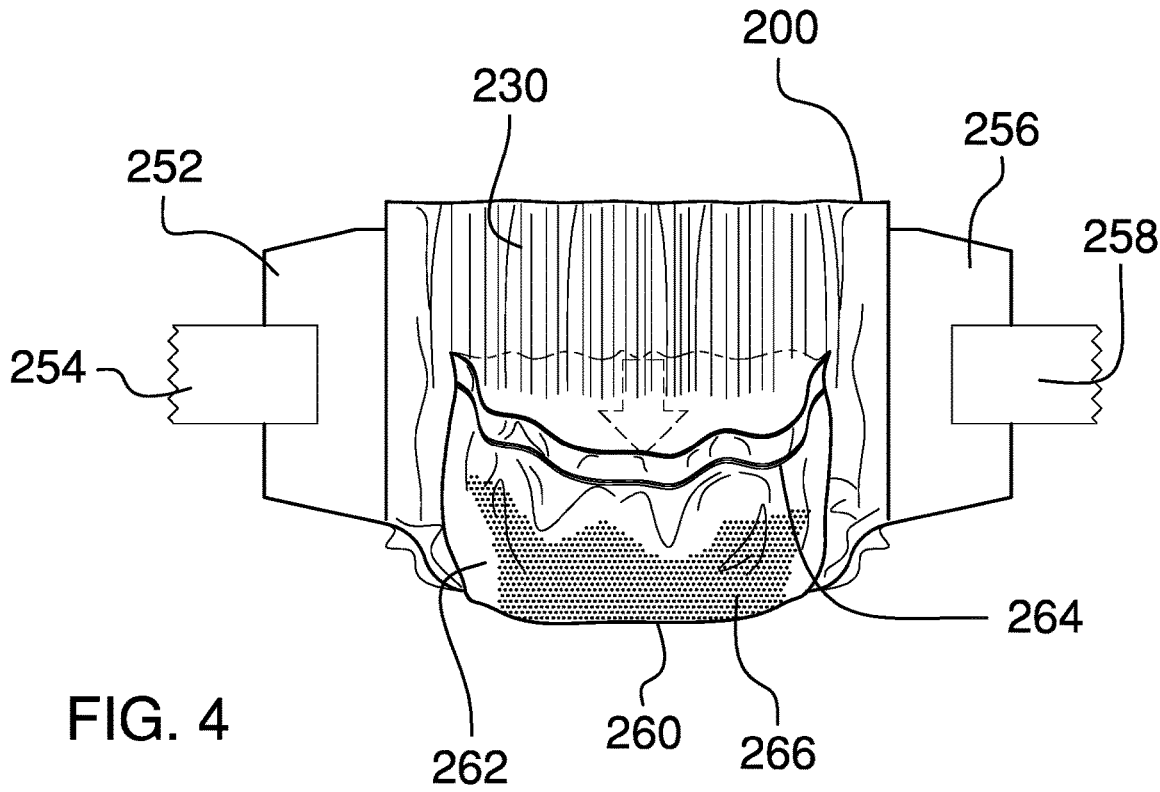
FIG. 4 is a rear view of an embodiment of the disclosure, aw worn, illustrating the step of pulling the elastic pouch band down on the rear side of the diaper.
Figure 5:
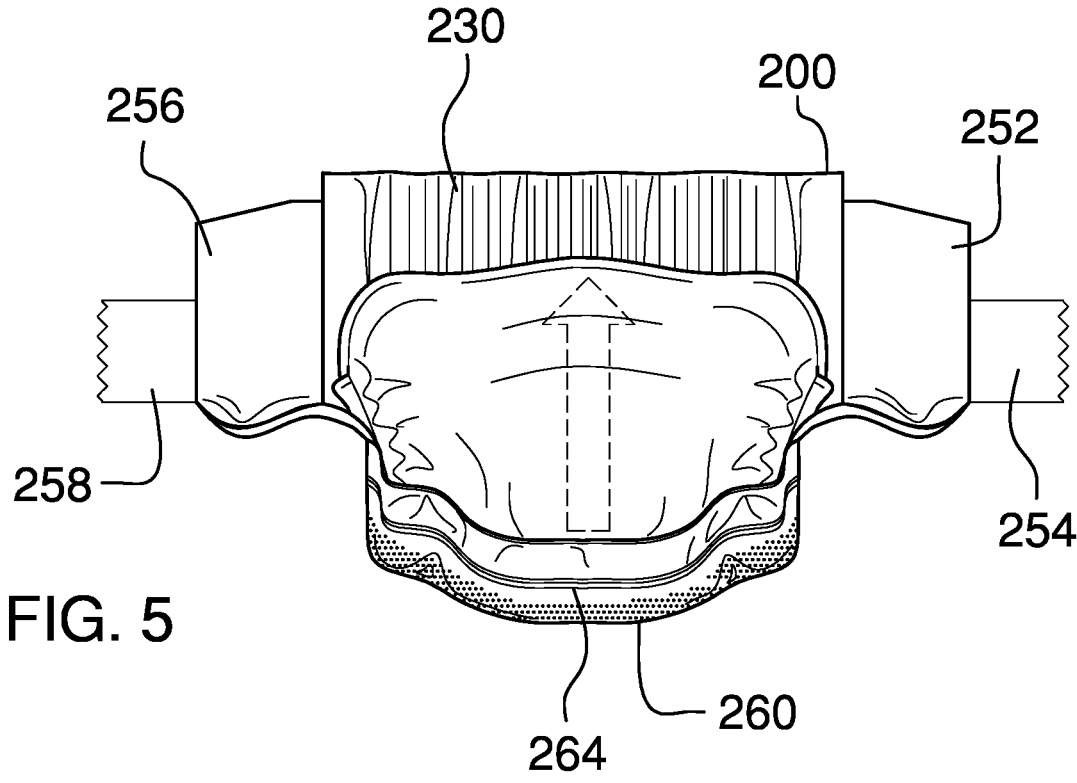
FIG. 5 is a front view of an embodiment of the disclosure, as worn, illustrating the step of pulling the disposal bag up over the front of the soiled diaper.
Figure 6:
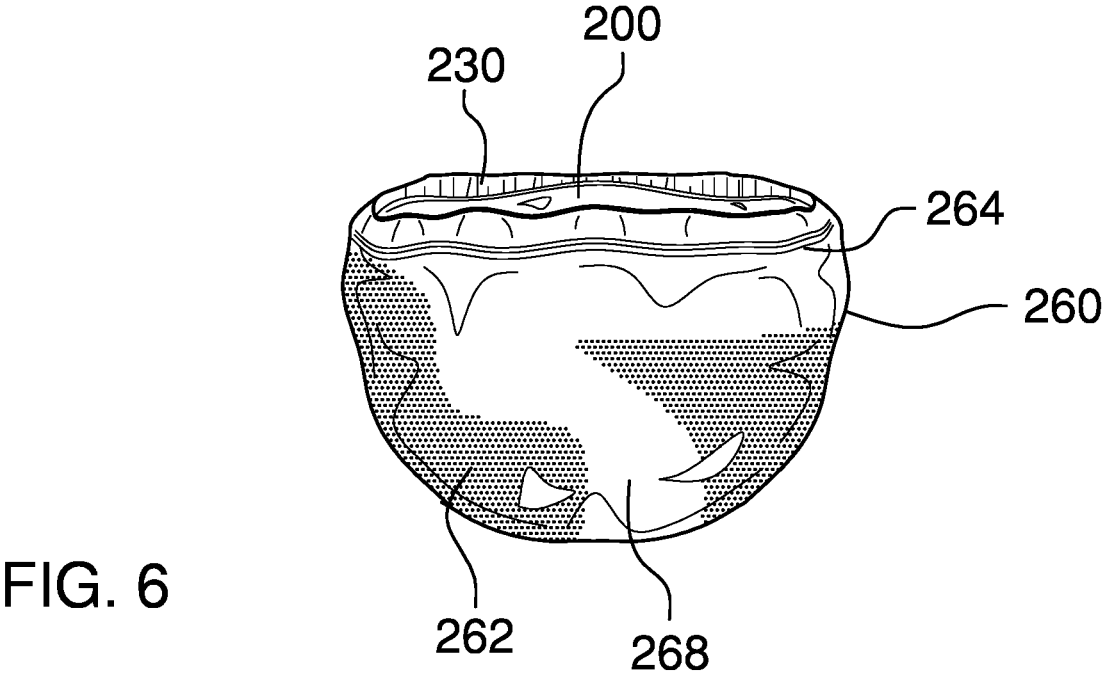
FIG. 6 is a front view of an embodiment of the disclosure, as worn, illustrating the step of pulling the elastic pouch band to the top of the soiled diaper thus enveloping the spoiled diaper.

Detailed reference will now be made to a first potential embodiment of the disclosure, which is illustrated in FIGS. 1 through 6.

The diaper with integrated disposal system 100 (hereinafter invention) comprises a disposable diaper 200 and a disposal bag 260. The disposable diaper 200 may be adapted to be worn by a baby to retain waste. As a non-limiting example, the waste may be urine and/or feces. The disposal bag 260 may be coupled to the outside of the back of the disposable diaper 200, as worn, such that the disposal bag 260 is kept clean and available at all times. The disposable diaper 200 containing the waste may be referred to as a soiled diaper. The soiled diaper may be removed from the baby and rolled to contain the waste. The disposal bag 260 may be pulled around the soiled diaper to seal the soiled diaper within the disposal bag 260.

Throughout this document, the phrase "as worn" may refer to the orientation, shape, and appearance of the disposable diaper 200 while the disposable diaper 200 is being worn by the baby. As a non-limiting example, FIG. 2 may represent the disposable diaper 200 "as worn".

The disposable diaper 200 may comprise a diaper core 210 and a plurality of waist wings. The diaper core 210 may be adapted to cover the genitals and buttocks of the baby by wrapping around the bottom of the baby's torso, between the baby's legs. The plurality of waist wings may couple around the baby's waist to hold the disposable diaper 200 in place. The diaper core 210 may be a multilayer pad that is operable to absorb the urine and confine the feces. The diaper core 210 may comprise a topsheet 220, an absorbent layer 222, a distribution layer 224, a storage layer 226, a backsheet 228, or any combination thereof.

The topsheet 220 may be the innermost layer of the disposable diaper 200. The topsheet 220 may be adapted to contact the baby. The topsheet 220 may be operable to pass the urine to the absorbent layer 222. As non-limiting examples, the central region of the topsheet 220 may be made from hydrophilic polypropylene to pass the urine and the edge of the topsheet 220, especially at a pair of leg cuffs, may be made of hydrophobic polypropylene to prevent leaks.

The absorbent layer 222 may be adapted to wick the urine away from the baby. As non-limiting examples, the absorbent layer 222 may be made from cellulose pulp fluff, polyester fibers, or any combination thereof.

The distribution layer 224 may be operable to direct the urine to the storage layer 226. As a non-limiting example, the distribution layer 224 may be made from nonwoven polypropylene.

The storage layer 226 may be adapted to absorb a large volume of the urine and to prevent the urine from returning to contact the baby. As non-limiting examples, the storage layer 226 may be made from SAP (super-absorbing polymers such as sodium polyacrylate) or a SAP/cotton blend.

The backsheet 228 may be the outermost layer of the disposable diaper 200. The backsheet 228 may be operable to prevent the urine from reaching clothing or bedding. As a non-limiting example, the backsheet 228 may be made from hydrophobic polyethylene film.

An elastic waistband 230 may be an elasticized area located at the top rear of the diaper core 210 as worn. The elastic waistband 230 may be operable to stretch in order to adjust the fit of the disposable diaper 200.

The pair of leg cuffs may comprise pre-formed bend areas at the center of both sides of the diaper core 210. A left leg cuff 232 selected from the pair of leg cuffs may be adapted to encircle the baby's left leg. A right leg cuff 234 selected from the pair of leg cuffs may be adapted to encircle the baby's right leg. In some embodiments, the pair of leg cuffs may comprise elastic material such that the fit of the pair of leg cuffs may retain the waste.

The plurality of waist wings may be lateral extensions of the diaper core 210 located at both ends of the diaper core 210. A pair of front waist wings selected from the plurality of waist wings may be located at the top of the front side of the disposable diaper 200 as worn. A pair of rear waist wings selected from the plurality of waist wings may be located at the top of the rear side of the disposable diaper 200 as worn. The pair of rear waist wings may be adapted to couple to the pair of front waist wings to encircle the baby's waist in order to retain the disposable diaper 200 on the baby. Specifically, a rear left waist wing 252 may comprise a rear left tape tab 254 that may be adhered to a front left waist wing 242 in order to couple the rear of the disposable diaper 200 to the front of the disposable diaper 200 on the left side of the disposable diaper 200. A rear right waist wing 256 may comprise a rear right tape tab 258 that may be adhered to a front right waist wing 244 in order to couple the rear of the disposable diaper 200 to the front of the disposable diaper 200 on the right side of the disposable diaper 200.

The rear left tape tab 254 and the rear right tape tab 258 may comprise pressure-sensitive tape that may be pressed against an individual waist wing selected from the pair of front waist wings to adhere to the individual waist wing and may be removed from the individual waist wing by pulling in a direction that is perpendicular to the surface of the individual waist wing. The rear left tape tab 254 and the rear right tape tab 258 may be reusable to seal the disposable diaper 200 multiple times.

The disposal bag 260 may be a waste disposal bag that is integral to the disposable diaper 200. The disposal bag 260 may comprise a pouch wall 262 and an elastic pouch band 264. The pouch wall 262 may be a hydrophobic panel coupled to the outside of the rear of the disposable diaper 200 along the bottom edge, left edge, and right edge, as worn. The pouch wall 262 may define an obverse side 266 and a reverse side 268. Prior to use, the obverse side 266 may be exposed and the reverse side 268 may be adjacent the backsheet 228. The top edge of the pouch wall 262, as worn, may be uncoupled to form an opening into a cavity located between the pouch wall 262 and the backsheet 228. As a non-limiting example, the pouch wall 262 may be made from the same material as the backsheet 228. The elastic pouch band 264 may be an elastic band coupled to the top edge of the pouch wall 262 in order to retract the top edge of the pouch wall 262.

The interior of the disposal bag 260 may be scented in order to mask odor emanating from the soiled diaper.

The soiled diaper may be disposed of by rolling the soiled diaper up from the front, as worn, by pulling the elastic pouch band 264 down from behind the soiled diaper, and then pulling the elastic pouch band 264 up on the front side of the soiled diaper until the soiled diaper is positioned inside of the disposal bag 260. The rear of the backsheet 228 and the reverse side 268 of the pouch wall 262 may comprise the exposed walls of the bagged soiled diaper. The disposal bag 260 will have been inverted from its initial configuration.

In use, the disposable diaper 200 may be placed on the baby by wrapping the diaper core 210 around the bottom of the baby's torso covering the genitals and the buttocks with the disposal bag 260 positioned behind the baby on the outside of the disposable diaper 200. The rear left tape tab 254 may be pulled forward and coupled to the front left waist wing 242 and the rear right tape tab 258 may be pulled forward and coupled to the front right waist wing 244. After the baby has urinated and/or defecated, the soiled diaper may be removed by uncoupling the rear left tape tab 254 and the rear right tape tab 258 and sliding the soiled diaper out from under the baby. The soiled diaper may be disposed of by rolling the soiled diaper up from the front, by pulling the elastic pouch band 264 down from behind the soiled diaper, and then pulling the elastic pouch band 264 up on the front side of the soiled diaper until the soiled diaper is positioned inside of the disposal bag 260. The bagged soiled diaper may be discarded into a trash receptacle.

Definitions

Unless otherwise stated, the words "up", "down", "top", "bottom", "upper", and "lower" should be interpreted within a gravitational framework. "Down" is the direction that gravity would pull an object. "Up" is the opposite of "down". "Bottom" is the part of an object that is down farther than any other part of the object. "Top" is the part of an object that is up farther than any other part of the object. "Upper" may refer to top and "lower" may refer to the bottom. As a non-limiting example, the upper end of a vertical shaft is the top end of the vertical shaft.

As used in this disclosure, a "cavity" may be an empty space or negative space that is formed within an object.

As used herein, the words "couple", "couples", "coupled" or "coupling", may refer to connecting, either directly or indirectly, and does not necessarily imply a mechanical connection.

As used in this disclosure, "disposable" may be an adjective that refers to an object that is designed and intended for a limited number of uses. In some cases, the object may be intended for a single use.

As used in this disclosure, "elastic" may refer to a material or object that deforms when a force is applied to stretch or compress the material and that returns to its relaxed shape after the force is removed. A material that exhibits these qualities is also referred to as an elastomeric material.

As used herein, "front" may indicate the side of an object that is closest to a forward direction of travel under normal use of the object or the side or part of an object that normally presents itself to view or that is normally used first. "Rear" or "back" may refer to the side that is opposite the front.

As used in this disclosure, the word "interior" may be used as a relational term that implies that an object is located or contained within the boundary of a structure or a space.

As used in this disclosure, the word "lateral" may refer to the sides of an object or movement towards a side. Lateral directions are generally perpendicular to longitudinal directions. "Laterally" may refer to movement in a lateral direction.

As used in this disclosure, "orientation" may refer to the positioning and/or angular alignment of a first object relative to a second object or relative to a reference position or reference direction.

As used herein, "superabsorbent polymer", or SAP, refers to a polymer that absorbs aqueous solutions through hydrogen bonding with water molecules. A superabsorbent polymer, also known as "slush power", may retain on the order of 300 times its dry weight in moisture. SAP may look like crystals or white sand when dehydrated and may appear to be gelatinous when hydrated. SAP is sometimes packaged within the layers of an outer cover, such as in a disposable diaper.

With respect to the above description, it is to be realized that the optimum dimensional relationship for the various components of the invention described above and in FIGS. 1 through 6, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A diaper with integrated disposal system comprising:
a disposable diaper and a disposal bag;
wherein the disposable diaper is adapted to be worn by a baby to retain waste, and mask odor;
wherein the disposal bag is coupled to the outside of the back of the disposable diaper, as worn, such that the disposal bag is kept clean and available at all times;
wherein a soiled diaper is removed and rolled to contain the waste;
wherein the disposal bag is pulled around the soiled diaper to seal the soiled diaper within the disposal bag;
wherein the disposal bag is a waste disposal bag that is integral to the disposable diaper;
wherein the disposal bag comprises a pouch wall and an elastic pouch band;
wherein the pouch wall is a hydrophobic panel coupled to the outside of the rear of the disposable diaper along a bottom edge, left edge, and right edge, as worn;
wherein the pouch wall defines an obverse side and a reverse side;
wherein prior to use, the obverse side is exposed and the reverse side is adjacent a backsheet;
wherein a top edge of the pouch wall, as worn, is uncoupled to form an opening into a cavity located between the pouch wall and the backsheet;
wherein the disposable diaper comprises a diaper core;
wherein the diaper core comprises a topsheet, an absorbent layer, a distribution layer, a storage layer, the backsheet, or any combination thereof;
wherein the pouch wall is made from the same material as the backsheet;
wherein the elastic pouch band is an elastic band coupled to the top edge of the pouch wall in order to retract the top edge of the pouch wall;
wherein the soiled diaper is disposed of by rolling the soiled diaper up from the front, as worn, by pulling the elastic pouch band down from behind the soiled diaper, and then pulling the elastic pouch band up on a front side of the soiled diaper until the soiled diaper is positioned inside of the disposal bag;
wherein the rear of the backsheet and the reverse side of the pouch wall comprise exposed walls of the bagged soiled diaper.

2. The diaper with integrated disposal system according to claim 1 wherein the disposable diaper comprises a plurality of waist wings;
wherein the diaper core is adapted to cover genitals and buttocks of the baby by wrapping around a bottom of the baby's torso, between a baby's legs;
wherein the plurality of waist wings is adapted to couple around the baby's waist to hold the disposable diaper in place;
wherein the diaper core is a multilayer pad that is operable to absorb urine and confine feces.

3. The diaper with integrated disposal system according to claim 2
wherein the topsheet is the innermost layer of the disposable diaper;
wherein the topsheet is adapted to contact the baby;
wherein the topsheet is operable to pass the urine to the absorbent layer.

4. The diaper with integrated disposal system according to claim 3 wherein the central region of the topsheet is made from hydrophilic polypropylene to pass the urine and the edge of the topsheet is made of hydrophobic polypropylene to prevent leaks.

5. The diaper with integrated disposal system according to claim 4 wherein the absorbent layer is adapted to wick the urine away from the baby.

6. The diaper with integrated disposal system according to claim 5 wherein the distribution layer is operable to direct the urine to the storage layer.

7. The diaper with integrated disposal system according to claim 6 wherein the storage layer is adapted to absorb the urine and to prevent the urine from returning to contact the baby.

8. The diaper with integrated disposal system according to claim 7 wherein the storage layer is made from super-absorbing polymers or a super-absorbing polymer/cotton blend.

9. The diaper with integrated disposal system according to claim 7 wherein the backsheet is the outermost layer of the disposable diaper;

wherein the backsheet is operable to prevent the urine from reaching clothing or bedding.

10. The diaper with integrated disposal system according to claim 9 wherein the backsheet is made from hydrophobic polyethylene film.

11. The diaper with integrated disposal system according to claim 9 wherein an elastic waistband is an elasticized area located at the top rear of the diaper core as worn;

wherein the elastic waistband is operable to stretch in order to adjust the fit of the disposable diaper.

12. The diaper with integrated disposal system according to claim 11 wherein a pair of leg cuffs comprise pre-formed bend areas at the center of both sides of the diaper core;

wherein a left leg cuff selected from the pair of leg cuffs is adapted to encircle the baby's left leg;

wherein a right leg cuff selected from the pair of leg cuffs is adapted to encircle the baby's right leg.

13. The diaper with integrated disposal system according to claim 12 wherein the pair of leg cuffs comprise elastic material such that the fit of the pair of leg cuffs retains the waste.

14. The diaper with integrated disposal system according to claim 12 wherein the plurality of waist wings are lateral extensions of the diaper core located at both ends of the diaper core;

wherein a pair of front waist wings selected from the plurality of waist wings are located at the top of the front side of the disposable diaper as worn;

wherein a pair of rear waist wings selected from the plurality of waist wings are located at the top of the rear side of the disposable diaper as worn;

wherein the pair of rear waist wings are adapted to couple to the pair of front waist wings to encircle the baby's waist in order to retain the disposable diaper on the baby;

wherein a rear left waist wing comprises a rear left tape tab that adheres to a front left waist wing in order to couple the rear of the disposable diaper to the front of the disposable diaper on the left side of the disposable diaper;

wherein a rear right waist wing comprises a rear right tape tab that adheres to a front right waist wing in order to couple the rear of the disposable diaper to the front of the disposable diaper on the right side of the disposable diaper.

15. The diaper with integrated disposal system according to claim 14 wherein the rear left tape tab and the rear right tape tab comprise pressure-sensitive tape that is pressed against an individual waist wing selected from the pair of front waist wings to adhere to the individual waist wing and is removed from the individual waist wing by pulling in a direction that is perpendicular to the surface of the individual waist wing;

wherein the rear left tape tab and the rear right tape tab are reusable to seal the disposable diaper multiple times.

16. The diaper with integrated disposal system according to claim 15 wherein the interior of the disposal bag is scented in order to mask odor emanating from the soiled diaper.

* * * * *